United States Patent [19]

Clavenna et al.

[11] Patent Number: 5,618,516
[45] Date of Patent: Apr. 8, 1997

[54] METHOD OF REDUCING SUBCUTANEOUS INFLAMMATION BY THE TOPICAL APPLICATION OF A HYDROPHILIC PHARMACEUTICAL COMPOSITION CONTAINING KETOPROFEN LYSINE SALT

[75] Inventors: Gaetano Clavenna, Rho Milano; Giorgio Poletti, Milan, both of Italy

[73] Assignee: Dompé Farmaceutici SpA, Milan, Italy

[21] Appl. No.: 622,362

[22] Filed: Mar. 25, 1996

Related U.S. Application Data

[62] Division of Ser. No. 199,972, Feb. 22, 1994, which is a continuation of Ser. No. 847,410, Mar. 6, 1992, abandoned.

[30] Foreign Application Priority Data

Mar. 6, 1991 [IT] Italy ................... MI91A0584

[51] Int. Cl.⁶ .................................... A61K 9/12
[52] U.S. Cl. ................. 424/45; 514/568; 514/570
[58] Field of Search ................ 424/45, 401, 405, 424/452; 514/568, 570

[56] References Cited

U.S. PATENT DOCUMENTS

| 4,282,216 | 8/1981 | Rovee et al. | 424/240 |
| 4,593,044 | 6/1986 | Metz | 514/557 |
| 4,954,332 | 9/1990 | Bissett et al. | 424/59 |

FOREIGN PATENT DOCUMENTS

| 882889 | 8/1980 | Belgium . |
| 58-010517 | 1/1983 | Japan . |
| 59-190912 | 10/1984 | Japan . |

OTHER PUBLICATIONS

Abstract # CA99 (24): 200431X; Pharmacokinetics of a Slow–Release Preparation of Ketoprofen Lysine in Man; Borsa et al.

Ketoprofen Penetration into Suction Skin Blister Fluid: A Comparison of Two Topical Formulations of Ketoprofen Lysine; Advances in Therapy, vol. 10 No. 2 Mar./Apr. 1993; pp. 86–94.

Farmacocinetica Di Ketoprofene Sale Di Lisina Dopo Applicazione Percutanea Della Formulazione Schiuma: Risultati Sperimentali E Clinici; Faramci vol. 16 No. 9–10/'92; pp. 1–11.

*Primary Examiner*—Neil S. Levy
*Attorney, Agent, or Firm*—Nikaido Marmelstein Murray & Oram LLP

[57] ABSTRACT

A hydrophile pharmaceutical composition in the form of foam is described which contains as active ingredient Ketoprofen lysine salt having a concentration between 10 and 20% p/volume of solution which allows, for topic treatment, the maximum absorption of the active principle. The foam is applied for the local treatment in painful and phlogistic conditions, of rheumatic or traumatic nature, of the articulations, of the musles, of the tendons and of the ligaments.

16 Claims, No Drawings

5,618,516

METHOD OF REDUCING SUBCUTANEOUS INFLAMMATION BY THE TOPICAL APPLICATION OF A HYDROPHILIC PHARMACEUTICAL COMPOSITION CONTAINING KETOPROFEN LYSINE SALT

This is a divisional of application Ser. No. 08/199,972 filed Feb. 22, 1994, pending which is a continuation of application Ser. No. 07/847,410 filed Mar. 6, 1992, now abandoned.

The object of the present invention relates to a topical pharmaceutical composition in the form of foam containing as active ingredient a compound having antiinflammatory activity which belongs to the class of the arylpropionic acids.

More particularly the arylpropionic acid contained in the composition object of the invention is represented by the lysine salt of the 2-(3-benzoylphenyl) propionic acid, known also as ketoprofen lysine salt, a compound which forms the object of the Italian Patent n$^0$1.104.556 in the name of the Applicant issued on 21st Oct. 1986.

The 2-(3-benzoylphenyl) propionic acid or ketoprofen, as the majority of the non-steroid antiinflammatories or FANS, derives its mechanism of action essentially from the inhibition of the biosynthesis of prostaglandines, prostacyclines and tromboxane. Compared to the ketoprofen, the ketoprofen lysine salt, even presenting a parallel pharmaceutical profile and a similar antiinflammatory-analgesic potency, offers the advantage of a considerably higher solubility in water and a greater gastric tolerability. The muscle-skeleton apparatus is particularly subject to possible physical trauma with a consequent formation of local inflammatory processes and therefore it is convenient to have at disposal compositions containing topical non-steroid antiinflammtory (FANS) drugs. The topical administration route is certainly the elective one for non-steroids antiinflammatory drugs, in case of local inflammatory processes because it minimizes the appearance of collateral effects, especially the gastric and renal ones, which appear during the therapy with the majority of such drugs.

With the exception of the drugs used for their surface topical effects, those which are applied on the skin have to penetrate the appropriate cutaneous layer to produce the therapeutical desired effect. The FANS, to work their action, have therefore to go through corneous layer and the vital part of the epidermis. The corneous layer, being a keratinized tissue, behaves like an artificial semipermeable membrane and the molecules of the drug penetrate by passive diffusion therefore according to the gradient of concentration. Therefore the speed of penetration through this cutaneous layer depends on the concentration of the drug in the carrier, on its solubility in water and its coefficient of distribution between the corneous layer and the carrier.

Therefrom it derives that in order that an antiinflammatory drug may have the desired effect it has to be administrated in elevated concentrations, thus it has to be contained in high concentrations in the pharmaceutical form for topical administration.

The topical pharmaceutical composition in the form of foam object of the present invention allows to obtain concentrations between 10 and 20%, of the ketoprofen lysine salt, being such concentrations not otherwise obtainable with other formulations, for example with the gel. A further advantage provided by the topical pharmaceutical composition of the invention is represented by the very low quantity therein contained of excipients which may, to some extent, interact with the skin. In particular said excipients, in the pharmaceutical composition in form of foam, totally amount to a percentage ranging from 5% to 10% p/volume of solution, with a very low content of alcoholic excipients, i.e. lower than 5%, while in the traditional pharmaceutical forms for topical use, such as gel or cream containing FANS, the percentages of alcoholic excipients are much higher and they may even reach 40% p/volume of solution.

The pharmaceutical composition in the form of foam contains 10–20% of a ketoprofen lysine salt solution, preferably 15% of ketoprofen lysine salt solution, and is emulsified, when erogated, by means of a suitable gas, for example, a mixture of butane, propane and isobutane gases, commonly denominated butane-propane, preferably mixed in the ratio butane:propane:isobutane=4:4:2, in a quantity from 3 up to 7% by weight of solution.

The quantity of a gaseous mixture corresponding to 5% by weight of the solution is particularly preferred. In the pharmaceutical composition in the form of foam are also included, other components such as a surfactant or an ionic or non-ionic emulsifier, an emollient substance, a thickener and optionally small quantities of a scent and of a bacteriostatic substance. As ionic emulsifier potassium laurylsulphate may be used and as non-ionic emulsifier non-ethoxylated derivatives such as sorbitan esters or ethers (SPAN) or ethoxylated derivatives such as, for example, polyoxyethylenesorbitan ethers or esters and polyoxymethylene ethers and esters (Cremophor, Myri) may be used. The quantity of the emulsifier is between 2 and 8% p/volume of solution. The quantity particularly preferred for ionic emulsifiers is between 2 and 3% p/volume of solution while for the non-ionic emulsifiers said quantity is between 3 and 5% p/volume of solution.

As an emollient substance propylene glycol, glycerin or polyethyleneglycols having a molecular weight between 300 and 3.000 (Carbowax of Polywax 300-1.500-3.000) may be used. The quantity of emollient varies from 2 to 6% p/volume of solution; quantities between 3 and 4% p/volume of solution are particularly preferred.

As a thickening substance, substituted amides of saturated or insaturated fatty acids of vegetable origin (Comprelan-Henkel); substituted and/or salified celluloses such as, for example, methylethylcellulose, sodium carboxymethylcellulose, methylcellulose, isopropylmethylcellulose; substituted vinyl pyrrolidone polymeres having different molecular weights such as, for example, polyvinylpyrrolidone K 30; carboxypolymethylene (Carbopol) may be used. The quantity of the thickener varies from 0.2 to 3% p/volume of solution. The scent optionally present may be constituted by nerolin lavender in a quantity from 0.05% to 0.2% p/volume of solution.

The bacteriostatic substance which, although not strictly necessary, can be present to assure the microbiological purity as time passes may be constitutd by benzoic acid and by its esters (Nipagin-Nipasol) or by benzilic alcohol and is added in a quantity from 0.1 to 0.5 p/volume of solution. The topical antiinflammatory pharmaceutical composition in the form of foam, object of the present invention, is of simple application and it is suitable for the local treatment of painful and phlogistic conditions, of rheumatic or traumatic nature, of the articulations of the musles, of the tendons and of the ligaments. A suitable posology foresees that, according to the area that has to be treated and of the entity of the inflammation, the foam be applied 2–3 times a day on the effected parts and made to penetrate by lightly rubbing.

The examples which follow are given only to illistrate, without limiting, the object of the invention.

EXAMPLE 1

Ketoprofen lysine salt (1.5 kg) is dissolved under stirring in depurated water (6.9 l).

In another container are placed:

Polysorbate 80 (0.4 kg); propylene glycol (0.4 kg); PVP K25 (polyvinylpyrrolidone) (0.3 kg); nerolin lavender (0.02 kg); benzilic alcohol (0.03 kg) and water q.s. to 1 liter.

The second solution is added, under stirring, to the first one and then, it is brought to volume (10 l) with water.

pH is controlled (range limits: 7–8.0). It is filtered under pressure and it is divided in small bottles. The valve is installed and secured to the small bottle. It is put in presure by loading butane-propane gas (5% by weight).

The final composition of the solution for 100 ml is the following:

| | |
|---|---|
| Ketoprofen lysine salt | 15.0 g |
| Polysorbate 80 | 4.0 g |
| Propylene glycol | 4.0 g |
| Polyvinylpyrrolidone (PVP K25) | 3.0 g |
| Nerolin lavender | 0.2 g |
| Benzilic alcohol | 0.3 g |
| Depurated water q.s. to | 100 ml |

EXAMPLE 2

Operation is carried out similarly to what described in Example 1 suitably varying the excipients and the following final composition is obtained:

| | |
|---|---|
| Ketoprofen lysine salt | 15.00 g |
| Laurylsulphate sodium | 2.00 g |
| Polyethyleneglycole (Carbowax 300) | 5.00 g |
| Sodium Carboxymethylcellulose b.v. | 0.25 g |
| Nerolin lavender | 0.20 g |
| Nipagin | 0.10 g |
| Nipasol | 0.02 g |
| Depurated water q.s. to | 100 ml |

EXAMPLE 3

Operation is carried out similarly to what described in Example 1 suitably varying the excipients and the following final composition is obtained:

| | |
|---|---|
| Ketoprofen lysine salt | 15.00 g |
| Span 20 | 5.50 g |
| Glycerin | 3.00 g |
| Hydroxypropylmethylcellulose E 3 | 0.35 g |
| Nerolin lavender | 0.20 g |
| Benzoic acid | 0.12 g |
| Depurated water q.s. to | 100 ml |

EXAMPLE 4

Operation is carried out similarly to what described in Example 1 suitably varying the excipients and the following final composition is obtained:

| | |
|---|---|
| Ketoprofen lysine salt | 15.00 g |
| Cremophor EL | 4.00 g |
| Propylene glycol | 4.00 g |
| Methylethylcellulose | 0.30 g |
| Nerolin lavender | 0.20 g |
| Nipagin | 0.12 g |
| Depurated water q.s. to | 100 ml |

EXAMPLE 5

Operation is carried out similarly to what described in Example 1 suitably varying the excipients and the following final composition is obtained:

| | |
|---|---|
| Ketoprofen lysine salt | 15.00 g |
| Myrj 52 | 5.00 g |
| Glycerin | 3.00 g |
| Polyvinylpyrrolidone K 30 | 4.00 g |
| Nerolin lavender | 0.15 g |
| Benzilic alcohol | 0.30 g |
| Depurated water q.s. to | 100 ml |

The absorption of the hydrophile solution of ketoprofen lysine salt was studied on female rabbits (New Zealand, 9–11 weeks) after topical administration of the composition in the form of foam at different concentrations (5%, 10%, 15% and 20%) having all the excipient composition as described in Example 1.

The foam was applied to 4 groups of rabbits (n=3) on the back, previously depilated (24 hours before the treatment), in an area of 100 cm$^2$ (10 cm×10 cm), at the dose of 10 mg/kg (average weight of animals 2000 g ±200 g).

The animals, immediately after the treatment, were put in metabolic cages. 2 ml of blood were taken at the following times: 0 (pre-dose), 15, 30, 60, 120, 240 and 360 minutes and urines were collected during the periods; 0–6 h, 6–12 h and 12–24 h after administration.

The determination of ketoprofen acid level in the plasma and urine was made by the HPLC method using as internal standard (IS) the Suprofen acid.

The samples of plasma, after IS adding were acidified with 1M potassium phosphate, pH=2.0 and extracted with ethyl ether. The urines after the IS adding underwent alkaline hydrolysis by 1N NaOH for 30 minutes, then neutralized by adding 1N HCl and finally acidified to pH=2.0 with 1M potassium phosphate and then extracted with ethyl ether. The ether phases of plasma and urine were evaporated to dryness under nitrogen. The residues of the plasma and urine extracts were taken up in 0.2M NH$_4$-formiate (pH=6.5) and injected in HPLC (volume of injection 20 µl).

The chromatography conditions are as follows:

Column: Merck Lichrospher 10RP-18 5 µm 125×4 mm with mobile phase pre-column: NH$_4$-formiate 0.2M pH (35% CH$_3$CN)

Flow rate: 1 ml/min

Detection: UV to 258 nm

The applied method is linear within the tested range 0.020–2 µg/ml (r$^2$ 0.99) for plasma and of 0.05–25 µg/ml (r$^2$ 0.99) for urines. The limit of the method is 0.01 µg/ml and the minimum concentration detectable is 0.05 µg/ml for both plasma and urine.

The administration in the rabbit of the hydrophile solution of ketoprofen lysine salt in the form of foam at 5%, 10%, 15% and 20% at the dose of 10 mg/kg does not determine in the plasma levels higher than the detectable limit of the method, while dosable levels of ketoprofen have been found in urines.

In Table 1 are shown the values of total excretion in each animal and the relative average (±DS). The FIG. 1 shows how after the application of the 5%, 10%, 15%, and 20% solutions there is an increase of the levels of ketoprofen in the urines which is proportional to the concentration of the active principle present in the composition.

The direct comparison between the concentrations of ketoprofen found in each period of urine collection and the concentrations of th active principle in the compositions was made with the Duncan test. The obtained risults show that the formulations containing 5%, 10% and 15% of ketoprofen lysine salt are each other statistically different (p 0.05), while it does not exist a statistical difference between the 15% formulation and the 20% one.

TABLE 1

Cumulative levels of ketoprofen acid after the application on the skin of a rabbit of 10 mg/kg of ketoprofen lysine salt foam at 5%, 10%, 15% and 20%.

| Collect- | Ketoprofen lysine salt foam at 5% Cumulative utine excretion (µg) | | | |
|---|---|---|---|---|
| ing time | 1 | 2 | 3 | Average ± SD |
| 0–6 h | 50 | 48 | 43 | 47 ± 4 |
| 6–12 h | 130 | 123 | 113 | 122 ± 9 |
| 12–24 h | 153 | 146 | 143 | 147 ± 5 |

| Collect- | Ketoprofen lysine salt foam 10% Cumulative urine excretion (µg) | | | |
|---|---|---|---|---|
| ing time | 4 | 5 | 6 | Average ± SD |
| 0–6 h | 126 | 122 | 121 | 123 ± 3 |
| 6–12 h | 261 | 268 | 256 | 262 ± 6 |
| 12–24 h | 286 | 296 | 275 | 286 ± 11 |

| Collect- | Ketoprofen lysine salt foam 15% Cumulative urine excretion (µg) | | | |
|---|---|---|---|---|
| ing time | 7 | 8 | 9 | Average ± SD |
| 0–6 h | 195 | 205 | 196 | 199 ± 6 |
| 6–12 h | 387 | 359 | 386 | 377 ± 16 |
| 12–24 h | 473 | 473 | 456 | 467 ± 10 |

| Collect- | Ketoprofen lysine salt foam 20% Cumulative urine excretion (µg) | | | |
|---|---|---|---|---|
| ing time | 10 | 11 | 12 | Average ± SD |
| 0–6 h | 198 | 205 | 208 | 204 ± 5 |
| 6–12 h | 381 | 390 | 406 | 392 ± 13 |
| 12–24 h | 471 | 490 | 487 | 483 ± 10 |

What we claim is:

1. A method of reducing inflammation of an inflamed subcutaneous area of the body which comprises:
   forming a composition comprising, by volume based on the total volume of the composition:
   at least about 67% water;
   0.2 to 3% thickening agent;
   less than 15 volume percent by volume of a liquid excipient, comprising:
   less than 5 volume percent of alcohol; and
   2 to 8% volume percent of at least one emulsifier; and
   12 to 18 percent by volume of a lysine salt of ketoprofen;
   forming an admixture of said composition with about 3 to 7 by weight, based on the weight of the entire admixture, of a propellant comprising at least one member selected from the group consisting of propane, butane and isobutane under sufficient pressure to prevent foaming thereof;
   topically applying said admixture to a skin area proximate to said subcutaneous inflammation under conditions sufficient to permit said composition to foam and to become applied to said skin as a foam form material; and
   causing at least lysine salt of ketoprofen to penetrate from said foam through said skin into effective engagement with the subcutaneous inflamed area of the body in an amount sufficient to have an anti-inflammatory effect thereon.

2. A method as claimed in claim 1 wherein said aqueous composition additionally contains: at least one emulsifier, and at least one emollient.

3. A method as claimed in claim 2 wherein said composition comprises 2 to 8 volume percent of said emulsifier.

4. A method as claimed in claim 2 wherein said emulsifier is a non-ionic emulsifier.

5. A method as claimed in claim 2 wherein said emulsifier is an ionic emulsifier.

6. A method as claimed in claim 2 wherein said composition comprises 3 to 4 volume percent of said emollient.

7. A method as claimed in claim 2 wherein said composition additionally comprises 0.05 to 0.2 volume percent of a scent.

8. A method as claimed in claim 2 wherein said composition additionally comprises 0.1 to 0.5 volume percent of a bacteriostat.

9. A method as claimed in claim 4 wherein said non-ionic emulsifier is at least one member selected from the group consisting of sorbitan esters, sorbitan ethers, polyoxymethylene esters, polyoxymethylene ethers, polyoxymethylene sorbitan esters, and polyoxymethylene sorbitan ethers.

10. A method as claimed in claim 5 wherein said ionic emulsifier is a lauryl sulfate.

11. A method as claimed in claim 2 wherein said emollient is at least one member selected from the group consisting of glycerine, propylene glycol, and polyethylene glycol.

12. A method as claimed in claim 2 wherein said thickener is at least one member selected from the group consisting of amides, cellulose, vinyl pyrrolidone polymers, and carboxypolymethylene.

13. A method as claimed in claim 2 wherein said bacteriostat is at least one member selected from the group consisting of benzoic acid, benzoic acid esters, and benzylic acid.

14. A method as claimed in claim 1 wherein said composition comprises about 15 volume percent of said ketoprofen lysine salt.

15. A method as claimed in claim 1 wherein said propellant gas comprises said butane, propane and isobutane in volumetric proportions relative to each other of 4:4:2.

16. A method as claimed in claim 1 wherein said propellant comprises 5 volume percent of said composition.

* * * * *